United States Patent [19]

King et al.

[11] 4,272,387
[45] * Jun. 9, 1981

[54] PROCESS OF PREPARING MOLYBDENUM COMPLEXES, THE COMPLEXES SO-PRODUCED AND LUBRICANTS CONTAINING SAME

[75] Inventors: John M. King, San Rafael; Louis de Vries, Greenbrae, both of Calif.

[73] Assignee: Chevron Research Company, San Francisco, Calif.

[ * ] Notice: The portion of the term of this patent subsequent to Apr. 21, 1998, has been disclaimed.

[21] Appl. No.: 52,699

[22] Filed: Jun. 28, 1979

[51] Int. Cl.$^3$ .............................................. C10M 1/54
[52] U.S. Cl. ................................ 252/46.4; 252/34.7; 252/46.7; 252/49.7; 252/400 R; 252/400 A; 260/125; 260/128; 260/137
[58] Field of Search ................... 252/34.7, 46.4, 49.7, 252/51, 25, 400 R, 400 A; 260/125, 128, 137

[56] References Cited

U.S. PATENT DOCUMENTS

| | | | |
|---|---|---|---|
| 3,140,997 | 7/1964 | Price | 252/25 X |
| 3,223,625 | 12/1965 | Cyphers et al. | 252/49.7 X |
| 3,281,355 | 10/1966 | Cyphers et al. | 252/25 X |
| 3,290,245 | 12/1966 | Elliott et al. | 252/49.7 X |
| 3,509,051 | 4/1970 | Farmer et al. | 252/46.4 X |
| 3,591,496 | 7/1971 | Vickars et al. | 252/25 X |
| 4,098,705 | 7/1978 | Sakurai et al. | 252/33.6 |
| 4,164,473 | 8/1979 | Coupland et al. | 252/42.7 X |
| 4,192,757 | 3/1980 | Brewster | 252/42.7 X |

FOREIGN PATENT DOCUMENTS

| | | | |
|---|---|---|---|
| 1076298 | 2/1960 | Fed. Rep. of Germany | 252/46.4 |
| 1095973 | 12/1960 | Fed. Rep. of Germany | 252/34.7 |
| 1085903 | 10/1967 | United Kingdom . | |
| 2037317A | 7/1980 | United Kingdom . | |

*Primary Examiner*—Andrew Metz
*Attorney, Agent, or Firm*—D. A. Newell; V. J. Cavalieri

[57] ABSTRACT

Antioxidant additives for lubricating oil are prepared by combining an acidic molybdenum compound, a basic nitrogen compound complex and a sulfur source to form a sulfur- and molybdenum-containing composition.

13 Claims, No Drawings

PROCESS OF PREPARING MOLYBDENUM COMPLEXES, THE COMPLEXES SO-PRODUCED AND LUBRICANTS CONTAINING SAME

FIELD OF THE INVENTION

This invention relates to new lubricating oil compositions. More specifically, it relates to new lubricating oil compositions containing antioxidant molybdenum compounds.

BACKGROUND OF THE INVENTION

Molybdenum disulfide has long been known as a desirable additive for use in lubricating oil compositions. However, one of its major detriments is its lack of oil solubility. Molybdenum disulfide is ordinarily finely ground and then dispersed in the lubricating oil composition to impart friction modifying and antiwear properties. Finely ground molybdenum disulfide is not an effective oxidation inhibitor in lubricating oils.

As an alternative to finely grinding the molybdenum disulfide, a number of different approaches involving preparing salts of molybdenum compounds have been tried. One type of compound which has been prepared is molybdenum dithiocarbamates. Representative compositions are described in U.S. Pat. No. 3,419,589, which teaches molybdenum (VI) dioxide dialkyldithiocarbamates; 3,509,051, which teaches sulfurized oxymolybdenum dithiocarbamates; and 4,098,705, which teaches sulfur containing molybdenum dihydrocarbyl dithiocarbamate compositions.

An alternative approach is to form dithiophosphates instead of dithiocarbamates. Represenatative of this type of molybdenum compound are the compositions described in U.S. Pat. No. 3,494,866, such as oxymolybdenum diisopropylphosphorodithioate.

U.S. Pat. No. 3,184,410 describes certain dithiomolybdenyl acetylacetonates for use in lubricating oils.

Braithwaite and Greene in Wear, 46 (1978) 405-432 describe various molybdenum-containing compositions for use in motor oils.

U.S. Pat. No. 3,349,108 teaches a molybdenum trioxide complex with diethylenetriamine for use as an additive for molten steel.

Russian Pat. No. 533,625 teaches lube oil additives prepared from ammonium molybdate and alkenylated polyamines.

Another way to incorporate molybdenum compounds in oil is to prepare a colloidal complex of molybdenum disulfide or oxysulfides dispersed using known dispersants. U.S. Pat. No. 3,223,625 described a procedure in which an acidic aqueous solution of certain molybdenum compounds is prepared and then extracted with a hydrocarbon ether dispersed with an oil soluble dispersant and then freed of the ether. U.S. Pat. No. 3,281,355 teaches the preparation of a dispersion of molybdenum disulfide by preparing a mixture of lubricating oil, dispersant, and a molybdenum compound in water or $C_{1-4}$ aliphatic alcohol, contacting this with a sulfide ion generator and then removing the solvent. Dispersants said to be effective in this procedure are petroleum sulfonates, phenates, alkylphenate sulfides, phosphosulfurized olefins and combinations thereof.

SUMMARY OF THE INVENTION

It has been found that a lubricating oil additive can be prepared by combining an acidic molybdenum compound, a basic nitrogen-containing composition, and a sulfur source, to form a molybdenum and sulfur combining complex.

DETAILED DESCRIPTION OF THE INVENTION

Lubricating oil compositions containing the additive prepared as disclosed herein are effective as either fluid and grease compositions (depending upon the specific additive or additives employed) for inhibiting oxidation, imparting antiwear and extreme pressure properties, and/or modifying the friction properties of the oil which may, when used as a crank-case lubricant, lead to improved mileage.

The precise molecular formula of the molybdenum compositions of this invention is not known with certainty; however, they are believed to be compounds in which molybdenum, whose valences are satisfied with atoms of oxygen or sulfur is either complexed by or the salt of one or more nitrogen atoms of the basic nitrogen containing compositions used in the preparation of these compositions.

The molybdenum compounds used to prepare the compositions of this invention are acidic molybdenum compounds. By acidic is meant that the molybdenum compounds will react with a basic nitrogen compound as measured by ASTM test D-664 or D-2896 titration procedure. Typically these molybdenum compounds are hexavalent and are represented by the following compositions: molybdic acid, ammonium molybdate, sodium molybdate, potassium molybdate and other alkaline metal molybdates and other molybdenum salts such as hydrogen salts, e.g. hydrogen sodium molybdate, $MoOCl_4$, $MoO_2Br_2$, $Mo_2O_3Cl_6$, molybdenum trioxide or similar acidic molybdenum compounds. Preferred acidic molybdenum compounds are molybdic acid, ammonium molybdate, and alkali metal molybdates. Particularly preferred are molybdic acid and ammonium molybdate.

The basic nitrogen compound must have a basic nitrogen content as measured by ASTM D-664 or D-2896. It is preferably oil-soluble. Typical of such compositions are succinimides, carboxylic acid amides, hydrocarbyl monoamines, hydrocarbon polyamines, Mannich bases, phosphonamides, thiophosphonamides, phosphoramides, dispersant viscosity index improvers, and mixtures thereof. These basic nitrogen-containing compounds are described below (keeping in mind the reservation that each must have at least one basic nitrogen). Any of the nitrogen-containing compositions may be after-treated with e.g., boron, using procedures well known in the art so long as the compositions continue to contain basic nitrogen. These after-treatments are particularly applicable to succinimides and Mannich base compositions.

The mono and polysuccinimides that can be used to prepare the lubricating oil additives described herein are disclosed in numerous references and are well known in the art. Certain fundamental types of succinimides and the related materials encompassed by the term of art "succinimide" are taught in U.S. Pat. Nos. 3,219,666, 3,172,892, and 3,272,746, the disclosures of which are hereby incorporated by reference. The term "succinimide" is understood in the art to include many of the amide, imide, and amidine species which are also formed by this reaction. The predominant product, however, is a succinimide and this term has been generally accepted as meaning the product of a reaction of an alkenyl subtituted succinic acid or anhydride with a nitrogen containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetraamine, and tetraethylene pentamine. Particularly preferred are those succinimides prepared from polyisobutenyl succinic anhydride of 70 to 128 carbon atoms and tetraethylene pentaamine or triethylene tetraamine or mixtures thereof.

Also included within the term succinimide are the cooligomers of a hydrocarbyl succinic acid or anhydride and a poly secondary amine containing at least one tertiary amino nitrogen in addition to two or more secondary amino groups. Ordinarily this composition has between 1,500 and 50,000 average molecular weight. A typical compound would be that prepared by reacting polyisobutenyl succinic anhydride and ethylene dipiperazine. Compositions of this type are disclosed in U.S. Ser. No. 816,063 filed July 15, 1977 the disclosure of which is hereby incorporated by reference.

Carboxylic amide compositions are also suitable starting materials for preparing the products of this invention. Typical of such compounds are those disclosed in U.S. Pat. No. 3,405,064, the disclosure of which is hereby incorporated by reference. These compositions are ordinarily prepared by reacting a carboxylic acid or anhydride or ester thereof, having at least 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula $R^2COOH$, where $R^2$ is $C_{12-20}$ alkyl or a mixture of this acid with a polyisobutenyl carboxylic acid in which the polyisobutenyl group contains from 72 to 128 carbon atoms and (2) an ethylene amine, especially triethylene tetraamine or tetraethylene pentaamine or mixtures thereof.

Another class of compounds which are useful in this invention are hydrocarbyl monoamines and hydrocarbyl polyamines, preferably of the type disclosed in U.S. Pat. No. 3,574,576, the disclosure of which is hereby incorporated by reference. The hydrocarbyl, which is preferably alkyl, or olefinic having one or two sites of unsaturation, usually contains from 9 to 350, preferably from 20 to 200 carbon atoms. Particularly preferred hydrocarbyl polyamines are those which are derived, e.g., by reacting polyisobutenyl chloride and a polyalkylene polyamine, such as an ethylene amine, e.g. ethylene diamine, diethylene triamine, tetraethylene pentaamine, 2-aminoethylpiperazine, 1,3-propylene diamine, 1,2-propylenediamine and the like.

Another class of compounds useful for supplying basic nitrogen are the Mannich base compositions. These compositions are prepared from a phenol or $C_{9-200}$ alkylphenol, an aldehyde, such as formaldehyde or formaldehyde precursor such as paraformaldehyde, and an amine compound. The amine may be a mono or polyamine and typical compositions are prepared from an alkylamine, such as methylamine or an ethylene amine, such as, diethylene triamine, or tetraethylene pentaamine. The phenolic material may be sulfurized and preferably is dodecylphenol or a $C_{80-100}$ alkylphenol. Typical Mannich bases which can be used in this invention are disclosed in U.S. Pat. No. 4,157,309, and U.S. Pat. Nos. 3,649,229, 3,368,972 and 3,539,663, the disclosures of which are hereby incorporated by reference. The last application discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1-10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the composition.

Another class of composition useful for preparing the additives of this invention are the phosphoramides and phosphonamides such as those disclosed in U.S. Pat. Nos. 3,909,430 and 3,968,157 the disclosures of which are hereby incorporated by reference. These compositions may be prepared by forming a phosphorus compound having at least one P-N bond. They can be prepared, for example, by reacting phosphorus oxychloride with a hydrocarbyl diol in the presence of a monoamine or by reacting phosphorous oxychloride with a difunctional secondary amine and a mono-functional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and nitrogen-containing compound as defined above, particularly an alkylamine, alkyldiamine, alkylpolyamine, or an alkyleneamine, such as ethylene diamine, diethylenetriamine, triethylenetetraamine, tetraethylenepentaamine, and the like.

Another class of nitrogen-containing compositions useful in preparing the molybdenum compositions of this invention includes the so-called dispersant viscosity index improvers (VI improvers). These Vi improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer then contacted with a nitrogen-containing source to introduce nitrogen-containing functional groups on the polymer backbone. Commonly used nitrogen sources include any basic nitrogen compound especially those nitrogen compounds and compositions described herein. Preferred nitrogen sources are alkylene amines, such as ethylene amines, alkyl amines, and Mannich bases.

Preferred basic nitrogen compounds for use in this invention are succinimides, carboxylic acid amides, and Mannich bases.

Representative sulfur sources are sulfur, hydrogen sulfide, sulfur monochloride, sulfur dichloride, phosphorus pentasulfide, $R_2S_x$ where R is hydrocarbyl, preferably $C_{1-40}$ alkyl, and x is at least 2, inorganic sulfides and polysulfides, such as $(NH_4)_2S_x$, where x is at least 1, thioacetamide, thiourea, and mercaptans of the formula RSH where R is as defined above. Also useful as sulfurizing agents are traditional sulfur-containing antioxidants such as wax sulfides and polysulfides, sulfurized olefins, sulfurized carboxylic and esters and sulfurized ester-olefins, and sulfurized alkylphenols and the metal salts thereof.

The sulfurized fatty acid esters are prepared by reacting sulfur, sulfur monochloride, and/or sulfur dichloride with an unsaturated fatty ester under elevated temperatures. Typical esters include $C_1$–$C_{20}$ alkyl esters of $C_8$–$C_{24}$ unsaturated fatty acids, such as palmitoleic, oleic, ricinoleic, petroselinic, vaccenic, linoleic, linolenic, oleostearic, licanic, paranaric, tariric, gadoleic, arachidonic, cetoleic, etc. Particularly good results have been obtained with mixed unsaturated fatty acid esters, such as are obtained from animal fats and vegetable oils, such as tall oil, linseed oil, olive oil, caster oil, peanut oil, rape oil, fish oil, sperm oil, and so forth.

Exemplary fatty esters include lauryl tallate, methyl oleate, ethyl oleate, lauryl oleate, cetyl oleate, cetyl linoleate, lauryl ricinoleate, oleyl linoleate, oleyl stearate, and alkyl glycerides.

Cross-sulfurized ester olefins, such as a sulfurized mixture of $C_{10}$–$C_{25}$ olefins with fatty acid esters of $C_{10}$–$C_{25}$ fatty afids and $C_1$–$C_{25}$ alkyl or alkenyl alcohols, wherein the fatty acid and/or the alcohol is unsaturated may also be used.

Sulfurized olefins are prepared by the reaction of the $C_3$–$C_6$ olefin or a low-molecular-weight polyolefin derived therefrom with a sulfur-containing compound such as sulfur, sulfur monochloride, and/or sulfur dichloride.

Also useful are the aromatic and alkyl sulfides, such as dibenzyl sulfide, dixylyl sulfide, dicetyl sulfide, diparaffin wax sulfide and polysulfide, cracked wax-olefin sulfides and so forth. They can be prepared by treating the starting material, e.g., olefinically unsaturated compounds, with sulfur, sulfur monochloride, and sulfur dichloride. Particularly preferred are the paraffin wax thiomers described in U.S. Pat. No. 2,346,156.

Sulfurized alkyl phenols and the metal salts thereof include compositions such as sulfurized dodecylphenol and the calcium salts thereof. The alkyl group ordinarily contains from 9–300 carbon atoms. The metal salt may be preferably, a group I or group II salt, especially sodium, calcium, magnesium, or barium.

Preferred sulfur sources are sulfur, hydrogen sulfide, phosphorous pentasulfide, $R_2S_x$ where R is hydrocarbyl, preferably $C_{1-10}$ alkyl, and x is at least 3, mercaptans wherein R is $C_{1-10}$ alkyl, inorganic sulfides and polysulfides, thioacetamide, and thiourea. Most preferred sulfur sources are sulfur, hydrogen sulfide, phosphorus pentasulfide, and inorganic sulfides and polysulfides.

A method for preparing compositions of this invention is to prepare a solution of the acidic molybdenum precursor with a basic nitrogen-containing compound with or without diluent. The diluent is used, if necessary, to provide a suitable viscosity for easy stirring. If desired, ammonium hydroxide may also be added to the reaction mixture to provide a solution of ammonium molybdate. This reaction is carried out at a temperature from the melting point of the mixture to reflux temperature. It is ordinarily carried out at atmospheric pressure although higher or lower pressures may be used if desired. This reaction mixture is treated with a sulfur source as defined above and the reaction mixture at a suitable pressure and temperature for the sulfur source to react with the acidic molybdenum and basic nitrogen compounds. In some cases, removal of water from the reaction mixture may be desirable prior to completion of reaction with the sulfur source.

In the reaction mixture, the ratio of molybdenum compound to basic nitrogen compound is not critical; however, as the amount of molybdenum with respect to basic nitrogen increases, the filtration of the product becomes more difficult. Since the molybdenum component probably oligomerizes, it is advantageous to add as much molybdenum as can easily be maintained in the composition. Usually, the reaction mixture will have charged to it from 0.01 to 2.00 atoms of molybdenum per basic nitrogen atom. Preferably from 0.4 to 1.0, and most preferably from 0.4 to 0.7, atoms of molybdenum per atom of basic nitrogen is added to the reaction mixture.

The sulfur source is usually charged to the reaction mixture in such a ratio to provide 0.1 to 4.0 atoms of sulfur per atom of molybdenum. Preferably from 0.5 to 3.0 atoms of sulfur per atom of molybdenum is added, and most preferably, 1.0 to 2.6 atoms of sulfur per atom of molybdenum.

The lubricating oil compositions containing the additives of this invention can be prepared by admixing, by conventional techniques, the appropriate amount of the molybdenum-containing composition with a lubricating oil. The selection of the particular base oil depends on the contemplated application of the lubricant and the presence of other additives. Generally, the amount of the molybdenum containing additive will vary from 0.05 to 15% by weight and preferably from 0.2 to 10% by weight.

The lubricating oil which may be used in this invention includes a wide variety of hydrocarbon oils, such as naphthenic bases, paraffin bases and mixed base oils as well as synthetic oils such as esters and the like. The lubricating oils may be used individually or in combination and generally have a viscosity which ranges from 50 to 5,000 SUS and usually from 100 to 15,000 SUS at 38° C.

In many instances it may be advantageous to form concentrates of the molybdenum containing additive within a carrier liquid. These concentrates provide a convenient method of handling and transporting the additives before their subsequent dilution and use. The concentration of the molybdenum-containing additive within the concentrate may vary from 0.25 to 90% by weight although it is preferred to maintain a concentration between 1 to and 50% by weight. The final application of the lubricating oil compositions of this invention may be in marine cylinder lubricants as in crosshead diesel engines, crankcase lubricants as in automobiles and railroads, lubricants for heavy machinery such as steel mills and the like, or as greases for bearings and the like. Whether the lubricant is fluid or a solid will ordinarily depend on whether a thickening agent is present. Typical thickening agents include polyurea acetates, lithium stearate and the like.

If desired, other additives may be included in the lubricating oil compositions of this invention. These additives include antioxidants or oxidation inhibitors, dispersants, rust inhibitors, anticorrosion agents and so forth. Also anti-foam agents stabilizers, anti-stain agents, tackiness agents, anti-chatter agents, dropping point improvers, anti-squawk agents, extreme pressure agents, odor control agents and the like may be included.

Certain molybdenum products that can be prepared by the process of invention also find utility in making brake lining materials, in high-temperature structural materials, in iron and steel alloys, in cladding materials, in electroplating solutions, as components for electrical discharge machine electrodes, as fuel additives, in making self-lubricating or wear-resistant structures, as mold release agents, in compositions for phosphatizing steel, in brazing fluxes, in nutrient media for microorganisms, in making electrosensitive recording material, in catalysts for refining coal, oil, shale, tar sands, and the like or as stabilizers or curing agents for natural rubber or polymers.

What is claimed is:

1. A process for preparing a sulfurized molybdenum-containing composition which comprises (1) reacting an acidic molybdenum compound and a basic nitrogen compound selected from the group consisting of a succinimide, carboxylic acid amide, Mannich base, phosphonamide, thiophosphonamide, phosphoramide, dispersant viscosity index improvers, or mixtures thereof, to form a molybdenum complex wherein from 0.01 to 2 atoms of molybdenum are present per basic nitrogen atom; and (2) reacting said complex with a sulfur containing compound, in an amount to provide 0.1 to 4.0 atoms of sulfur per atom of molybdenum, to form a sulfur- and molybdenum-containing composition.

2. The process of claim 1 wherein the sulfur source is sulfur, hydrogen sulfide, phosphorus pentasulfide, $R_2S_x$ where R is hydrocarbyl, and x is at least 2, inorganic sulfides, inorganic polysulfides, thioacetamide, thiourea, mercaptan of the formula RSH where R is hydrocarbyl, or a sulfur-containing antioxidant.

3. The process of claim 2 wherein the sulfur source is sulfur, hydrogen sulfide, phosphorus pentasulfide, $R_2S_x$ where R is $C_{1-40}$ hydrocarbyl, and x is at least 3, an inorganic sulfide, or inorganic polysulfide, thioacetamide, thiourea or RSH where R is $C_{1-40}$ alkyl, and the acidic molybdenum compound is molybdic acid, ammonium molybdate, or an alkali metal molybdate.

4. The process of claim 3 wherein said sulfur source is sulfur, hydrogen sulfide, RSH where R is $C_{1-10}$ alkyl, phosphorus pentasulfide, or $(NH_4)_2S_{x'}$, where $x'$ is at least 1, said acidic molybdenum compound is molybdic acid or ammonium molybdate, and said basic nitrogen compound is a succinimide, carboxylic acid amide, or Mannich base.

5. The process of claim 4 wherein said basic nitrogen compound is a $C_{24-350}$ hydrocarbyl suffinimide, carboxylic acid amide, or a Mannich base prepared from a $C_{9-200}$ alkylphenol, formaldehyde, and an amine.

6. The process of claim 5 wherein said basic nitrogen compound is a polyisobutenyl succinimide prepared from polyisobutenyl succinic anhydride and tetraethylene pentaamine or triethylene tetraamine.

7. The process of claim 5 wherein said basic nitrogen compound is a carboxylic acid amide prepared from one or more carboxylic acids of the formula $R^2COOH$, or a derivative thereof which upon reaction with an amine yields a carboxylic acid amide, wherein $R^2$ is $C_{12-350}$ alkyl or $C_{12-350}$ alkenyl and a hydrocarbyl polyamine.

8. The process of claim 7 wherein $R^2$ is $C_{12-20}$ alkyl or $C_{12-20}$ alkenyl and the hydrocarbyl polyamine is tetraethylene pentaamine or triethylene tetraamine.

9. The process of claim 6 wherein said basic nitrogen compound is a Mannich base prepared from dodecylphenol, formaldehyde, and methylamine.

10. The process of claim 6 wherein said basic nitrogen compound is a Mannich base prepared from $C_{80-100}$ alkylphenol, formaldehyde and triethylene tetraamine, tetraethylene pentaamine, or mixtures thereof.

11. The product prepared by the process of claim 1, 2, 3, 4, 5, 6, 7, 8, 9, or 10.

12. A lubricating oil composition comprising an oil of lubricating viscosity and from 0.05 to 15% by weight of the product of claim 11.

13. A concentrate comprising an oil of lubricating viscosity and from 0.25 to 90% by weight of the product of claim 11.

* * * * *